United States Patent [19]
Vollmer et al.

[11] 3,998,764
[45] Dec. 21, 1976

[54] REDUCING FLAMMABILITY OF POLYURETHANE FOAMS WITH PHOSPHORUS COMPOUNDS

[75] Inventors: Hartfrid Vollmer, Erftstadt Liblar; Franz-Josef Dany, Erftstadt Lechenich; Joachim Wortmann, Turnich, all of Germany

[73] Assignee: Hoechst Aktiengesellschaft, Frankfurt am Main, Germany

[22] Filed: Nov. 6, 1974

[21] Appl. No.: 521,501

[30] Foreign Application Priority Data

Nov. 9, 1973    Germany .................... 2356033

[52] U.S. Cl. .............. 260/2.5 AJ; 260/2.5 AR; 260/45.7 P; 260/928; 260/929; 260/930
[51] Int. Cl.² ............. C08G 18/14; C08G 18/38; C08G 18/32
[58] Field of Search ............ 260/2.5 AR, 2.5 AJ, 260/45.7 P

[56] References Cited
UNITED STATES PATENTS

| | | | |
|---|---|---|---|
| 3,332,893 | 7/1967 | Birum et al. | 260/2.5 AR |
| 3,433,856 | 3/1969 | Friedman | 260/2.5 AR |
| 3,737,397 | 6/1973 | Baranauckas et al. | 260/2.5 AR |
| 3,850,859 | 11/1974 | Wortmann et al. | 260/2.5 AJ |
| 3,882,199 | 5/1975 | Batorewicz | 260/2.5 AR |

*Primary Examiner*—H.S. Cockeram
*Attorney, Agent, or Firm*—Connolly and Hutz

[57] ABSTRACT

Production of agents reducing the flammability of polyurethane moulding compositions. The agents are more particularly comprised of compounds of the following general formula (I)

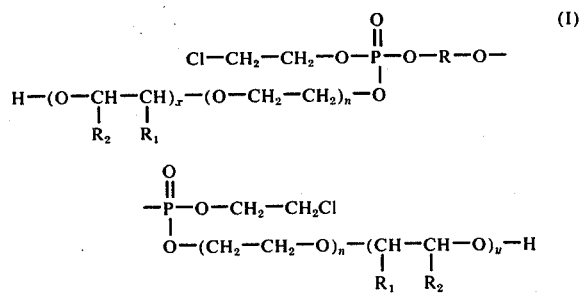

in which R stands for an alkylene radical having from 2 to 6 carbon atoms, which may be halogen-substituted, if desired, a $-CH_2-CH_2-O-CH_2-CH_2-$ radical, a phenylene radical or an alkyl- or halogenoalkyl-substituted diphenylene methane radical, $R_1$ and $R_2$, respectively, stand for a hydrogen atom, an alkyl radical or a halogen-substituted alkyl radical having from 1 to 4 carbon atoms, $x + y$ stand for a number between 0.1 and 3, and $n$ stands for 1 or 2.

4 Claims, No Drawings

REDUCING FLAMMABILITY OF POLYURETHANE FOAMS WITH PHOSPHORUS COMPOUNDS

The present invention relates to novel agents reducing the flammability of polyurethane moulding compositions, and to a process for making them.

Polyurethanes, particularly polyurethane foam plastics, find widespread uses in industry for a plurality of purposes, and they are still gaining interest. On account of their excellent heat and sound-absorbing properties, polyurethane foam plastics are widely used, for example, in the building industry, as heat insulators in refrigerators and cars, pipelines, tanks, tank cars, and for a plurality of further purposes. A particularly beneficial effect which polyurethanes offer is the ease with which they can be produced on the spot. Polyurethane soft plastics are widely employed in commercial quantities for the manufacture of mattresses, upholstery for furniture and automobile seats, and for many other uses.

To be suitable for these uses, it is often necessary or at least desirable for the polyurethanes to have satisfactory flameproofing properties.

Various attempts have already been made to render polyurethanes difficultly inflammable, commonly by adding a phosphorus-containing flameproofing agent thereto. In those cases, however, in which these addends are merely incorporated with the plastics, they are likely to migrate or become extracted therefrom, under outdoor conditions, especially if polyurethane foam plastics are concerned.

Typical representatives of the above addends are, for example: tris-(dichloropropyl)-phosphate, tris-(dibromopropyl)-phosphate or ethylene-bis-(2-chloroethyl)-phosphonate of the following formula

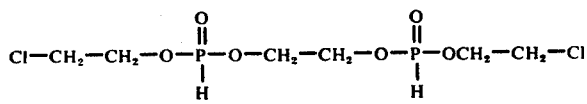

this latter compound having been disclosed in U.S. Pat. No. 3,147,299, Example 2.

Reactive flameproofing agents, which are chemically combined with the plastics, are, however, not likely to migrate therefrom. Particularly well adapted for use as flameproofing agents in polyurethanes are phosphorus-containing polyols, such as those described in U.S. Pat. No. 3,220,961. As described in Example 4 of that specification, a compound of the following formula:

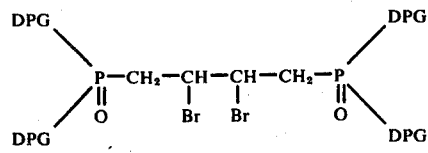

in which DPG stands for dipropylene glycol, can be used as a reactive flameproofing agent for polyurethane foam plastics.

We have now found that it is possible for the flameproofing effect produced by the above reactive flameproofing agent in polyurethane foam plastics to be improved by modifying the constitution of the agent described in U.S. Pat. No. 3,147,299, Example 2, i.e., by substituting an organic radical containing OH—-groups for the hydrogen atoms which are linked to the phosphorus atom, and using the agent so modified as the flameproofing agent.

The present invention relates more particularly to agents reducing the flammability of polyurethane moulding compositions, the agents comprising compounds of the following general formula (I)

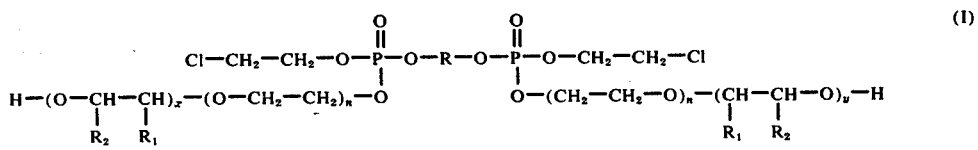

in which R stands for an alkylene radical having from 2 to 6 carbon atoms, which may be halogen-substituted, if desired, a —CH$_2$—CH$_2$—O—CH$_2$—CH$_2$— radical, a phenylene radical or an alkyl- or halogenoalkyl-substituted diphenylene methane radical, R$_1$ and R$_2$, respectively, stand for a hydrogen atom, an alkyl radical or a halogen-substituted alkyl radical having from 1 to 4 carbon atoms, $x + y$ stand for a number between 0.1 and 3, and $n$ stands for 1 or 2.

In the above formula (I), R preferably stands for an ethylene or hexamethylene radical, a radical of the following formula

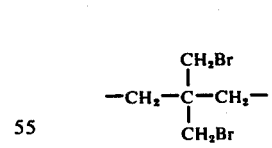

or a radical of the following formula

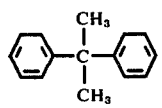

The agents of the present invention are preferably comprised of the following compounds (a) – (k), which are highly viscous, colorless and undistillable liquids of the following formulae:

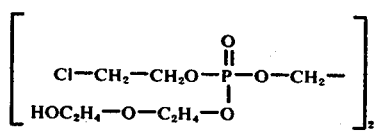 a)
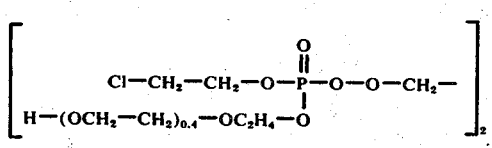 b)
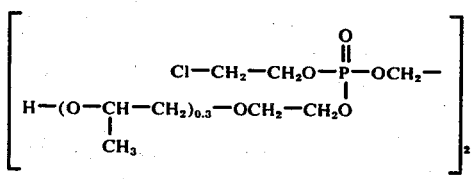 c)
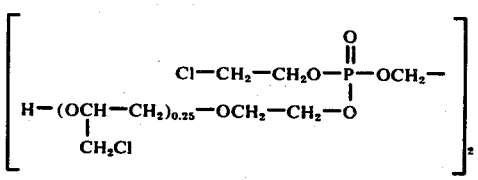 d)
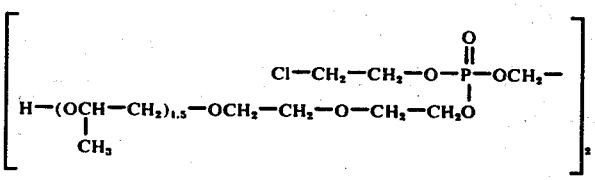 e)
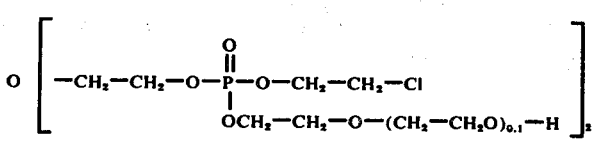 f)
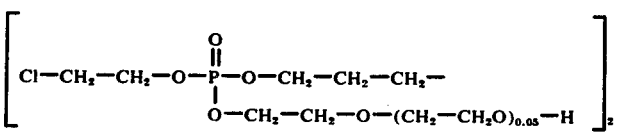 g)
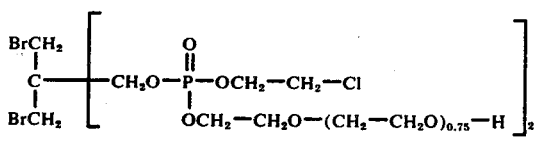 h)
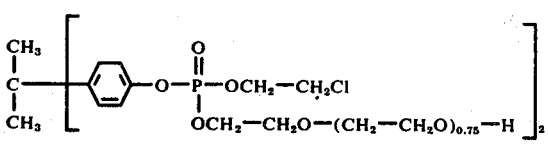 i)

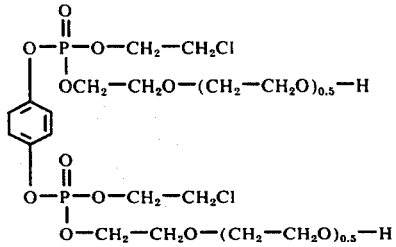

The invention also relates to a process for making polyurethane moulding compositions of reduced flammability by subjecting an organic polyol and a flameproofing agent containing alcoholic OH-groups to condensation with equivalent quantities of an organic isocyanate compound, if desired, in the presence of one or more activators, expanding agents and/or cell regulators, which comprises using as the flameproofing agent a compound of general formula (I)

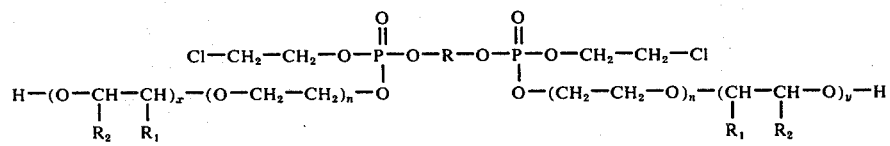

in which R stands for an alkylene radical having from 2 to 6 carbon atoms, which may be halogen-substituted, if desired, a —$CH_2$—$CH_2$—O—$CH_2$—$CH_2$— radical, a phenylene radical or an alkyl- or halogenoalkyl-substituted diphenylene methane radical, $R_1$ and $R_2$, respectively, stand for a hydrogen atom, an alkyl radical or a halogen-substituted alkyl radical having from 1 to 4 carbon atoms, $x + y$ stand for a number between 0.1 and 3, and $n$ stands for 1 or 2.

In the above formula (I), the substituent R stands preferably for an ethylene or hexamethylene radical, a radical of the following formula:

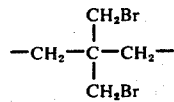

or a radical of the following formula:

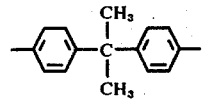

The polyurethane moulding composition should preferably contain the flameproofing agent in proportions substantially within the range 3 and 40 weight %, more preferably 5 and 15 weight %, based on the quantity of organic polyol, which may be a polyetherpolyol or polyesterpolyol free from halogen and phosphorus. It is possible, for example, to use a partially branched polyetherpolyol which is based on propylene oxide and has a hydroxyl number of 46 mg of KOH/g, a molecular weight of 3500 and a viscosity of 575 centipoises at 25° C.

The polyurethane moulding compositions of the present invention preferably contain as their isocyanate component 2,4- and/or 2,6-toluylene diisocyanate or diphenylmethane-4,4-diisocyanate. The addends, such as activators, expanding agents and cell regulators,

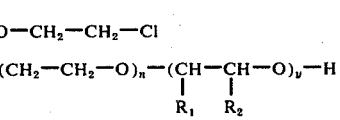

which are required to be used in the manufacture of polyurethane moulding compositions have already been described in the art. Tertiary amines and/or organo-tin compounds can be used as activators, chlorofluoroalkanes and/or water can be used as expanding agents, and polysiloxanes, preferably polyethylene-polydimethylsiloxane block copolymers, can be used as cell regulators.

The present agents reducing the flammability of polyurethane moulding compositions can be made by a process which comprises reacting a compound of the general formula (II)

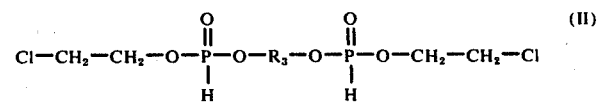

in which $R_3$ stands for an alkylene radical having from 2 to 6 carbon atoms, which may be halogen-substituted, if desired, a —$CH_2$—$CH_2$—O—$CH_2$—$CH_2$— radical, a phenylene radical or an alkyl- or halogenoalkyl-substituted diphenylenemethane radical, with at least stoichiometric proportions of chlorine gas, at temperatures within the range about 0° and 5° C, in the presence of a solvent, wherein hydrogen chloride gas is difficultly soluble, and thereby transforming the formula (II) compound into a compound of the general formula (III)

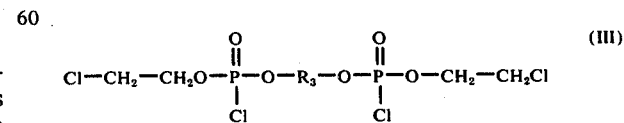

completing the reaction and removing then the chlorine gas in excess or resulting hydrogen chloride by introducing an inert gas into the reaction solution; and, while the introduction of inert gas is continued, admixing the reaction solution dropwise at temperatures within the range about 15° and 40° C with stoichiometric proportions of a diol of the general formula (IV)

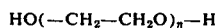  (IV)

in which n stands for 1 or 2; terminating the reaction; distilling off the solvent and subjecting the resulting product of the general formula (V)

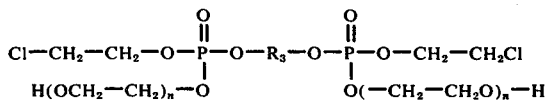

in which n and $R_3$ have the meanings given hereinabove, to epoxidation with at least stoichiometric proportions of a compound of the general formula (VI)

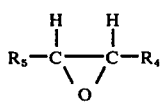  (VI)

in which $R_4$ and $R_5$, respectively, stand for a hydrogen atom, an alkyl radical or a halogen-substituted alkyl radical having from 1 to 4 carbon atoms, at temperatures within the range about 60° and 140° C for as long a period as necessary to provide for a continuous epoxide reflux; and separating epoxide in excess by distillation or by the introduction of an inert gas.

The intermediate compound of general formula (III) should preferably be produced in the presence of methylene chloride or dichloroethane which are solvents absorbing relatively slight proportions of the resulting hydrogen chloride gas byproduct. Fractions of hydrogen chloride, which may have been dissolved therein, can be removed therefrom, for example, by the introduction of nitrogen.

The formula (II) compound used as starting material in the process of the present invention has already been described in the art and can be produced, for example, by the process described in U.S. Pat. No. 3,147,299, Examples 1 and 2.

The agents of the present invention are commercially interesting reactive flameproofing agents for polyurethane foam plastics, which are more effective than compounds of similar constitution, such as the brominated diphosphonate of the following formula:

$$\left[ (HO-\underset{\underset{CH_3}{|}}{C}H-CH_2-O-\underset{\underset{CH_3}{|}}{C}H-CH_2O)_2-\overset{\overset{O}{\|}}{P}-CH_2-\underset{\underset{Br}{|}}{C}H- \right]_2$$

described in U.S. Pat. No. 3,220,961, Example 24.

The following Examples illustrate the invention, which is not limited thereto. Examples 1 to 4 illustrate the preparation of the agents of the present invention and Example 5 illustrates their efficiency in moulding compositions based on polyurethane foam plastics.

EXAMPLE 1

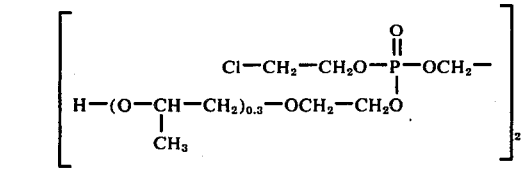

A reactor provided with reflux condenser and stirrer was charged with a solution of 2720 g of $PCl_3$ (19.8 mols) in 4 liters of methylene chloride and the solution was admixed dropwise with agitation and at room temperature with 1224 g of ethylene glycol (19.8 mols). The reaction was terminated after about 2 hours. A further 9.9 mols of ethyleneglycol was added in such a manner that the reaction temperature remained within the limits 20° and 25° C. Chlorine was then introduced into the solution at temperatures within the range 0° and 5° C until the solution assumed a green-yellow coloration, which indicated that the reaction was complete. Chlorine in excess and hydrogen chloride, which was found to have been formed, were expelled by the introduction of nitrogen into the solution. The introduction of nitrogen was continued and 1175 g of ethylene glycol was added dropwise at room temperature. After HCl ceased to be evolved, the solution was distilled so as to remove the solvent, and a highly viscous colorless liquid was obtained in a yield of 94.5 % of the theoretical.

1000 g of the colorless liquid so obtained was admixed with 2 g of $Na_2HPO_4$ and the whole was treated with propylene oxide at temperatures within the range 80° and 100° C for as long a period as necessary to have a continuous reflux which indicated that propylene oxide ceased to be absorbed. The reaction mixture was freed from volatile constituents by distilling it and 1090 g of a colorless product which had an acid number of less than 1 mg of KOH/g of substance was obtained. This corresponded to the absorption of about 0.6 mol of propylene oxide per mol of substance.

The product so made was analyzed and the following results were obtained:

|    | Found: | Calculated: |
|----|--------|-------------|
| P  | 12.4 % | 13.1 %      |
| OH | 6.5 %  | 7.5 %       |

EXAMPLE 2

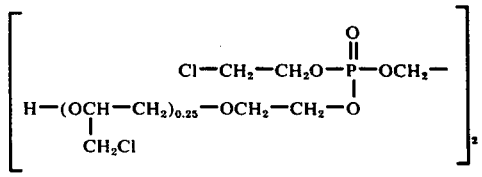

The procedure was the same as that described in Example 1, save that 600 g of the intermediary product was admixed with 1 g of $Na_2HPO_4$ and the whole was reacted with 65 g of epichlorhydrin at temperatures within the range 120° and 135° C. Volatile constituents were distilled off from the reaction mixture and 660 g of a colorless oil remained behind. This corresponded to the absorption of 0.5 mol of epichlorhydrin per mol of substance. The product had an acid number of 1 mg of KOH/g substance. It was analyzed and the following results were obtained:

|    | Found: | Calculated: |
|----|--------|-------------|
| P  | 12.6 % | 12.9 %      |
| Cl | 18.2 % | 18.2 %      |
| OH | 8.2 %  | 7.2 %       |

EXAMPLE 3

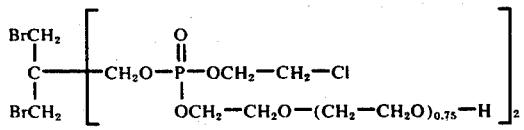

A solution of 10 mols of 2-chloro-1,3,2-dioxaphospholane in 2 l of methylene chloride was admixed with 5 mols of dibromoneopentyl glycol in such a manner that the reaction temperature did not exceed 20° C. Following this, chlorine gas was introduced until green-yellow coloration of the reaction solution indicated the end of the reaction. Chlorine in excess and hydrogen chloride which was found to have been produced were expelled by means of nitrogen. 570 g (1.3 mols) of the intermediate product dissolved in methylene chloride was reacted, while nitrogen was introduced thereinto, with 165 g of ethylene glycol (2.6 mols) at room temperature, and resulting hydrogen chloride was expelled. The solvent was then distilled off, the residue was admixed with 1 g of $Na_2HPO_4$ and epoxidized with ethylene oxide at about 90° C. 12 g of ethylene oxide were found to have been absorbed. This corresponded to the absorption of about 1.5 mols of ethylene oxide per mol of substance.

The product was analyzed and the following results were obtained:

|    | Found: | Calculated: |
|----|--------|-------------|
| P  | 8.0 %  | 8.8 %       |
| Cl | 9.2 %  | 10.1 %      |

EXAMPLE 4

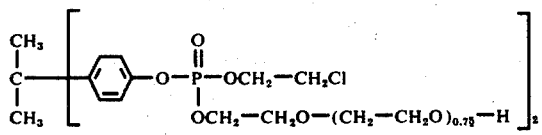

The procedure was the same as that described in Example 3, save that 228 g of p,p'-isopropylidene diphenol (1 mol) was dissolved in methylene chloride and 253 g of 2-chloro-1,3,2-dioxaphoxpholane (2 mols) was added dropwise to the solution. As the reaction proceeded, the solution became increasingly clear. The reaction temperature was within the range 25° and 35° C. At temperatures within the range −5° and +5° C, chlorine gas was introduced into the solution until it commenced to assume a yellow coloration.

0.8 mol of the intermediary product dissolved in methylene chloride was reacted at room temperature with 1.6 mols of ethylene glycol while nitrogen was introduced thereinto. Following this, the solvent was distilled off and the whole was epoxidized at 100° C with ethylene oxide with the addition of 1 g of $Na_2HPO_4$. Ethylene oxide was absorbed at a rate of 1.5 mols per mol of substance.

The product so made had an acid number of less than 1 mg of KOH/g substance.

It was analyzed and the following results were obtained:

|    | Found: | Calculated: |
|----|--------|-------------|
| P  | 8.9 %  | 9.3 %       |
| Cl | 11.8 % | 10.3 %      |
| OH | 7.6 %  | 5.1 %       |

EXAMPLE 5

The flameproofing efficiency of the products made in the manner described in Examples 1 to 4 was tested. To this end, they were incorporated with polyurethane soft foams and the foams were subjected to burn-up tests (ASTM D 1692-59 T). Comparative tests were made on known flameproofing agents, such as tris-(dichloropropyl)-phosphate, tris-(dibromopropyl)-phosphate, tetra-(dipropylene-glycol)-2,3-dibromobutene-1,4-diphosphonate and ethylene-bis-(2-chloroethyl)-phosphonate. The polyurethane soft foams were made as follows:

| | |
|---|---|
| 100 g | of a partially branched polyetherpolyol based on propylene oxide and having a hydroxyl number of 46 mg of KOH/g, a molecular weight of 3500, a viscosity of 575 centipoises at 25° C and a ratio of primary to secondary OH-groups of 22:78 (Desmophen 3800, a product of Bayer, Leverkusen), |
| 10 g | of flameproofing agent, |
| 4.2 g | of water, |
| 0.12 g | of triethylene diamine, |
| 0.2 g | of tin-II-octoate, and |
| 1.0 g | of a polyethylene-polydimethylsiloxane block copolymer having a viscosity of 1200 centistokes and a unit weight of 1.03 (L 540, a product of Union Carbide) | were blended together, and 53.2 g of toluylene diisocyanate (a 80:20 blend of the 2,4- and 2,6-isomers) was added to the blend so made, with rapid agitation. After about 20 seconds, the blend commenced foaming. It was poured in a container. After a certain expansion period, the foam began to harden. It was hard after storage for 15 minutes at 80° C. The foams so made were tested as to their flammability (ASTM D 1692-59 T). Both freshly prepared foams and foams artificially aged by 7-day exposure at 80° C and 100 % relative atmospheric moisture were tested. The results obtained are indicated in the following Table.

TABLE

| Flameproofing agent | I | II | III | |
|---|---|---|---|---|
| A | 90 | SE 34 mm, 29 sec | SE 26 mm, | 9 sec |
| B | 92 | SE 30 mm, 18 sec | SE 25 mm, | 11 sec |
| C | 84 | SE 41 mm, 23 sec | SE 40 mm, | 19 sec |
| D | 95 | SE 38 mm, 29 sec | SE 32 mm, | 9 sec |
| E | 85 | SE 64 mm, 44 sec | B 114 mm/min | |
| F | 90 | SE 46 mm, 37 sec | SE 62 mm, | 41 sec |
| G | 110 | SE 42 mm, 28 sec | SE 69 mm, | 43 sec |
| H | 70 | SE 30 mm, 16 sec | SE 45 mm, | 23 sec |

In the above Table, the various abbreviations have the following meanings:

Flameproofing agents:
A: Product of Example 1
B: Product of Example 2
C: Product of Example 3
D: Product of Example 4
E: Tris-(dichloropropyl)-phosphate
F: Tris-(dibromopropyl)-phosphate
G: Tetra-(dipropyleneglycol)-2,3-dibromobutene 1,4-diphosphonate (U.S. Pat. No. 3,220,961, Example 4)
H: Ethylene-bis-(2-chloroethyl)-phosphite (U.S. Pat. No. 3,147,299, Example 2)
Column I: Expansion period of foam in seconds
Column II: Burn-up test (ASTM D 1692-59 T) immediately after preparation of foam.
Column III: Burn-up test (ASTM D 1692-59 T) after storage of foam for 7 days at 80° C and 100 % relative atmospheric moisture.
SE: Self-extinction after . . . mm and . . . seconds
B: Burn-up rate in mm per minute As can be seen, the foams rendered flameproof with the agents of the present invention all have a shorter burn-up period until self-extinction than the foams rendered flameproof with known flameproofing agents. In other words, the flameproofing agents of the present invention compare favorably with the prior art agents.

EXAMPLE 6

A polyurethane rigid foam was prepared by blending the following substances together in the sequential order indicated, and pouring the resulting blend in a card board container.

| | | |
|---|---|---|
| 100 | g | of the polyetherpolyol of Example 5, |
| 5 | g | of the flameproofing agent C, |
| 4 | g | of water, |
| 0.15 | g | of triethylenediamine, |
| 0.18 | g | of tin-II-octoate, |
| 1 | g | of a polyethylene-polydimethylsiloxane block copolymer having a viscosity of 1200 centistokes at 25° C and a unit weight of 1.03 (L 540, a product of Union Carbide), and |
| 52 | g | of toluylene diisocyanate (a 80:20 blend of the 2,4-and 2,6-isomers). |

After 12 seconds, the blend began to expand over a period of 90 seconds and an open-pore flameproof foam was obtained.

EXAMPLE 7

A polyurethane soft foam was prepared by blending the following substances together in the sequential order indicated, and pouring the resulting blend in a card board container.

| | | |
|---|---|---|
| 100 | g | of the polyetherpolyol of Example 5, |
| 40 | g | of the flameproofing agent D, |
| 3 | g | of water, |
| 0.2 | g | of triethylenediamine, |
| 0.18 | g | of tin-II-octoate, |
| 1.5 | g | of the polyethylene-polydimethylsiloxane block copolymer of Example and |
| δ | g | of toluylene diisocyanate (a 80:20 blend of the 2,4-and 2,6-isomers). |

After 22 seconds, the blend began to expand over a period of 105 seconds and produce a foam.

EXAMPLE 8

A polyurethane soft foam was prepared by blending the following substances together in the sequential order indicated, and pouring the blend in a card board container.

| | | |
|---|---|---|
| 100 | g | of a oolyesterpolyol prepared from adipic acid and diethyleneglycol and having an OH-number of 60 mg of KOH/g, a viscosity of 20 000 centipoises at 25° C and a molecular weight of 2 000, |
| 10 | g | of the flameproofing agent A, |
| 1.3 | g | of dimethylbenzylamine, |
| 4.7 | g | of water, |
| 1 | g | of trichlorofluoromethane, |
| 1 | g | of the polyethylene-polydimethylsiloxane block copolymer of Example 6, and |
| 52 | g | of toluylene diisocyanate (a 80:20 blend of the 2,4- and 2,6-isomers). |

After 15 seconds, the blend commenced to expand over 85 seconds. An open-pore soft foam was obtained.

EXAMPLES 9–16

8 polyurethane rigid foams containing different proportions of flameproofing agent were prepared by blending the following substances and a flameproofing agent together.

100 g of a polyetherpolyol prepared by propoxylating a glycerol/sucrose mixture and having a hydroxyl number of 520 mg of KOH/g, a molecular weight of 350 and a viscosity of 6 000 centipoises at 20° C (Caradol 520, a product of Deutsche Shell-Chemie, Frankfurt),
1 g of water,
24 g of trichlorofluoromethane,
3 g of triethylamine,
1 g of the polyethylene-polydimethylsiloxane block copolymer of Example 6, and
150 g of methylenediphenyl-4,4'-diisocyanate.

The individual rigid foams contained the following flameproofing agents in the following quantities.

| Rigid foam of Example | Flameproofing agent | Quantity of flameproofing agent in grams |
|---|---|---|
| 9 | A | 10 |
| 10 | A | 20 |
| 11 | B | 10 |
| 12 | B | 20 |
| 13 | C | 10 |
| 14 | C | 20 |
| 15 | D | 10 |
| 16 | D | 20 |

After 14 and 26 seconds, respectively, the foams commenced to expand over periods between 90 and 125 seconds and closedcell rigid foams were obtained.

The polyurethane foams produced in the manner described in Examples 6 to 16 were tested as to their flammability (ASTM D 1692-59 T). The tests were made on the freshly prepared foams. The test results obtained are indicated in the following table:

TABLE II

| Polyurethane foam of Example | Burn-up behaviour |
|---|---|
| 6 | SE 68 mm, 49 sec. |
| 7 | SE 12 mm, 8 sec. |
| 8 | SE 23 mm, 12 sec. |
| 9 | SE 21 mm, 13 sec. |
| 10 | SE 16 mm, 7 sec. |
| 11 | SE 20 mm, 10 sec. |
| 12 | SE 16 mm, 5 sec. |
| 13 | SE 23 mm, 15 sec. |
| 14 | SE 19 mm, 11 sec. |
| 15 | SE 23 mm, 13 sec. |
| 16 | SE 18 mm, 9 sec. |

In the above Table, the abbreviation SE stands for self-extinction.

We claim:

1. A process for making polyurethane moulding compositions of reduced flammability by subjecting an organic polyol and a flameproofing agent containing alcoholic OH-groups to condensation with equivalent quantities of an organic isocyanate compound, in the presence of activators, expanding agents and cell regulators, which comprises using as the flameproofing agent a compound of general formula (I)

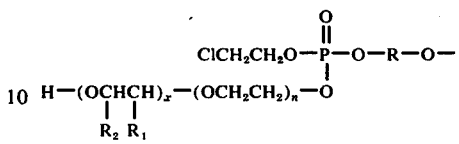

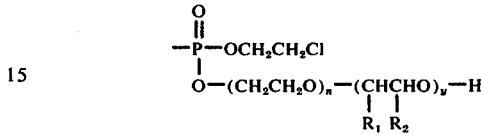

in which R represents phenylene, or alkyl- or halogen-alkyl-substituted diphenylene methane, $R_1$ and $R_2$, respectively, stand for a hydrogen atom, an alkyl radical or a halogen-substituted alkyl radical having from 1 to 4 carbon atoms, $x + y$ stand for a number between 0.1 and 3, and $n$ stands for 1 or 2.

2. The process as claimed in claim 1, wherein R stands for a radical of the formula:

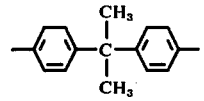

3. The process as claimed in claim 1, wherein the polyurethane moulding composition contains the flameproofing agent in a proportion within the range 3 and 40 weight %, based on the quantity of organic polyol.

4. The process as claimed in claim 3 wherein the proportion of flameproofing agent is within the range 5 and 15 weight %.

* * * * *